United States Patent
Derda et al.

(10) Patent No.: US 9,958,437 B2
(45) Date of Patent: May 1, 2018

(54) METHOD OF QUANTIFYING PEPTIDE-DERIVATIVE LIBRARIES USING PHAGE DISPLAY

(71) Applicant: The Governors of the University of Alberta, Edmonton (CA)

(72) Inventors: Ratmir Derda, Edmonton (CA); Simon Ng, Edmonton (CA); Seyed Mohammadreza Jafari, Edmonton (CA)

(73) Assignee: The Governors of the University of Alberta (CA)

( * ) Notice: Subject to any disclaimer, the term of this patent is extended or adjusted under 35 U.S.C. 154(b) by 360 days.

(21) Appl. No.: 14/375,939

(22) PCT Filed: Feb. 1, 2013

(86) PCT No.: PCT/CA2013/050083
§ 371 (c)(1),
(2) Date: Jul. 31, 2014

(87) PCT Pub. No.: WO2013/113127
PCT Pub. Date: Aug. 8, 2013

(65) Prior Publication Data
US 2015/0024958 A1    Jan. 22, 2015

Related U.S. Application Data

(60) Provisional application No. 61/594,593, filed on Feb. 3, 2012.

(51) Int. Cl.
*C12N 15/10* (2006.01)
*G01N 33/53* (2006.01)
*G01N 33/68* (2006.01)

(52) U.S. Cl.
CPC ......... *G01N 33/53* (2013.01); *C12N 15/1037* (2013.01); *G01N 33/68* (2013.01)

(58) Field of Classification Search
None
See application file for complete search history.

(56) References Cited

U.S. PATENT DOCUMENTS

| | | | |
|---|---|---|---|
| 5,733,757 A | 3/1998 | Barbas, III et al. | |
| 6,017,732 A | 1/2000 | Jespers et al. | |
| 6,642,014 B1 | 11/2003 | Pedersen et al. | |
| 7,141,366 B1 | 11/2006 | Sandman et al. | |
| 2009/0137424 A1 | 5/2009 | Tsao et al. | |
| 2010/0317547 A1 | 12/2010 | Gregory et al. | |

FOREIGN PATENT DOCUMENTS

WO    0105950 A2    1/2001

OTHER PUBLICATIONS

Love et al (2006 ChemBioChem 7:753-6).*
Geoghegan et al (1992 Bioconjugate Chemistry 3:136-46).*
Ng, S. et al. "Bacteriophages and Viruses as a Support for Organic Synthesis and Combinatorial Chemistry", ACS Chemical Biology, vol. 7, Oct. 11, 2011, 123-128.
Ng, S. et al. "Quantitative Synthesis of Genetically Encoded Glycopeptide Libraries Displayed on M13 Phage", ACS Chemical Biology, vol. 7, Jun. 24, 2012, 1482-1487.
International Search Report and Written Opinion related to Application No. PCT/CA2013/050083, dated May 10, 2013.
Eldridge, GM and Weiss, GA, "Hydrazide Reactive Peptide Tags for Site-Specific Protein Labeling." Bioconjugate Chemistry. 22:2143-2153, 2011.
Derda R, et al. "High-throughput Discovery of Synthetic Surfaces that Support Proliferation of Pluripotent Cells." J. Am. Chem. Soc. 132:1289-1295, 2010.
Supplementary European Search Report (EPO Form 1507S) corresponding to Application No. EP 13743260, dated Jul. 10, 2015, (7 pgs.).
Love et al. "A Facile Substrate Attachment Strategy for Phage Display Evolution of Glycosyltransferases" ACS Chem Bio Chem 7:753-756, 2006 (Supplemental Information Only—5 pages).
Ng et al., "Quantitative Synthesis of Genetically Encoded Glycopeptide Libraries Displayed on M13 Phage" ACS Chem Biol 2012, 7, 1482-1487 (with Supplemental Information—pp. S-1 to S-22).

* cited by examiner

*Primary Examiner* — Christopher M Gross
(74) *Attorney, Agent, or Firm* — Loeb & Loeb LLP

(57) ABSTRACT

The present application provides a method of quantifying an amount of a derivatized peptide displayed on a phage by phage display, the method comprising: providing a phage containing the target peptide thereon; reacting the phage containing the target peptide with a first reagent to derivatize the target peptide to form a derivatized peptide, reacting the derivatized peptide with a capture agent comprising a detection marker, thereby incorporating the detection marker within the derivatized peptide; and determining an amount of the detection marker, thereby quantifying the amount of the derivatized peptide displayed on the phage. A kit comprising a capture agent comprising a detection marker for quantifying the phage displayed derivatized peptides is also provided.

4 Claims, 18 Drawing Sheets

AcMet = N-acetyl methionine, MBT = 4-methoxybenzenethiol, GSH = glutathione, DTT = dithiothreitol.

METHOD OF QUANTIFYING PEPTIDE-DERIVATIVE LIBRARIES USING PHAGE DISPLAY

This application is the national phase of International Application No. PCT/CA13/050083, filed Feb. 1, 2013, entitled "Method of Quantifying Peptide-Derivative Libraries Using Phage Display," which claims the benefit of U.S. Provisional Application No. 61/594,593, filed Feb. 3, 2012, entitled, "Method and System for Synthesis of Libraries of Genetically-Encoded Peptide Derivatives," the disclosures of which are all incorporated by reference in their entirety.

FIELD

The present application pertains to the field of recombinant protein technology. More particularly, the present application relates to a method of quantifying derivatized peptide libraries using phage display.

BACKGROUND

The generation of libraries of small molecules and selection of those molecules that bind uniquely to a target of interest is important for drug discovery. The production of genetically-encoded libraries, in which each library member is linked to an information template, such as DNA or RNA, makes it possible to process large chemical libraries without separating individual library members into individual solutions and reaction vessels. One can select target molecules from mixtures of genetically-encoded molecules and identify or amplify the selected molecule of interest using its information template.

Phage display is one example of a genetically-encoded library. Phage display is a well known technique used in the analysis, display and production of protein antigens, especially human proteins of interest. Phage display is a process during which the phage, a bacterial virus, is made to expose or "display" different peptides or proteins including human antibodies on its surface. Through genetic engineering, peptides or proteins of interest are attached individually to a phage cell surface protein molecule (usually Gene III protein, g3p). In such a phage population (phage library), each phage carries a gene for a different peptide or protein—g3p fusion and exposes it on its surface. Through a variety of selection procedures, phages that "display" binders to specific target molecules of interest can be identified and isolated. These binders can include interaction partners of a protein to determine new functions or mechanisms of function of that protein, peptides that recognize and bind to antigens (for use in diagnosis and therapeutic targeting, for example), and proteins involved in protein-DNA interactions (for example, novel transcription factors).

The phage display technique can be very useful in discovery and development of pharmaceutical and/or diagnostic products. In phage display the entire phage binds and can be eluted from an immobilized target molecule. Since the phage remains infective it can inject its DNA into bacterial cells and is amplified. The main limitation of phage display, however, is the occurrence of non-specific adsorption of phages during the binding stage, which necessitates enrichment over several rounds and individually tailored washing and elution conditions. Phage display methods are usually restricted to the production of libraries, which can be encoded by direct DNA-RNA-protein information transfer. These methods are typically limited to linear sequences of peptides, made of only 20 natural amino acids.

Typically, the amplification of libraries of peptides on the surface of the phage requires an in vitro translation system, in which DNA is modified to express the displayed peptides of interest. The generation and use of such translation systems can be expensive and time consuming. The use of self-replicating species such as phage or bacteria simplifies amplification of libraries because each library member is amplified "spontaneously", when given the appropriate resources. For example, for phage displayed libraries, adding one phage to a simple culture broth with bacteria can produce an arbitrarily large population of phage for a very low cost.

Several methods exist which involve conversion of libraries of phage-displayed polypeptides to libraries of peptide derivatives. Typically, these methods use organic synthesis on the peptides to make peptide derivatives. The characterization and improvement of reaction yields is an important cornerstone of organic synthesis. Bulk biochemical methods, such as western blot and mass spectrometry, are often used, to quantify the amount of product obtained or to determine the success of generating the desired reaction products. However, in the absence of this characterization, the synthesis cannot be claimed to be reliable or reproducible. Reactions used for synthesis of such libraries of peptide derivatives have typically been validated using one phage clone or one purified peptide. The actual synthesis of libraries is typically done "blindly", and the efficiency of such synthesis is unknown. The quality of the libraries generated by this method is, thus, usually unknown. While selection from these libraries can provide useful non-peptidic molecules, overall the efficiency of such selection is unclear.

Jesper at al. in U.S. Pat. No. 6,017,732, describe chemical modification of point residues in antibodies displayed on phagemid. This patent discusses a limited set of reactions including the alkylation of a Cys residue within an antibody, and subsequent detection with fluorescence and radioactive probes. The technique described in Jesper is designed for estimating the yield in large ($>10^{10}$ copies) clonal populations of phage. However, there is no teaching or suggestion of the quantification or optimization of a derivative library synthesis.

U.S. Pat. No. 7,141,366 to Noren et al, describes the production of phage with a unique chemical residue, selenocysteine (Sec), incorporated in a specific location in a phage-displayed peptide. Phage-displayed peptide libraries that contain Sec were generated, thus creating modified peptide libraries. Bulk biochemical methods, such as western blot, were used to qualitatively characterize the chemical modifications that occur on the Sec residue. However, this method cannot be extended to Sec-free peptide libraries, and, further, there is no teaching or suggestion of the quantification or optimization of a derivative library synthesis.

US Patent Publication 2009/0137424 to Schultz et al, describes the production of phage with non-natural amino-acids incorporated at a specific location within a phage-displayed peptide using orthogonal tRNA and aminoacyl tRNA synthase. Phage-displayed peptide libraries that contain azido phenyl alanine (AzPhe) are generated. Bulk biochemical methods, such as western blot and mass spectrometry, are used to qualitatively characterize the chemical modifications that occur on AzPhe residues. No methods for quantification of chemical yields in single or multi-step reactions in the synthesis of the library are described, nor strategies for improvement of chemical yields.

U.S. Pat. No. 6,642,014 to Pedersen et al, describes the use of capture agents to select enzymes with improved or new activities. This patent discusses the generation of chemicals by enzyme catalysis, not by direct chemical transformation. Specially-engineered phagemid is used and required to display both enzyme and substrate on the surface of phage.

US Patent Publication 2010/0317547 to Winter and Heinis, describes methods for the generation of a library of bicyclic peptides displayed on phage from a linear peptide, which contains random amino acids flanked by three cysteine residues.

Typically, and as indicated in the above references, the phage display methods known in the art are not designed for efficiency and success of the reactions during synthesis. These previous systems are often characterized on purified protein from phage well after the derivatizing reaction has taken place. The yields of reactions on phage, and the quality and purity of the library are, thus, generally unknown.

Thus, there remains a need for quantitative characterization of peptide-derivative phage display to determine the quality of the phage display procedure and a corresponding optimization of the procedure to ensure optimal yields of reaction products.

This background information is provided for the purpose of making known information believed by the applicant to be of possible relevance to the present application. No admission is necessarily intended, nor should be construed, that any of the preceding information constitutes prior art against the present invention.

SUMMARY

An object of the present application is to provide a method of quantifying peptide-derivative libraries using phage display.

In accordance with one aspect of the present invention, there is provided a method of quantifying an amount of a derivatized peptide displayed on a phage by phage display, the method comprising: providing a phage containing a target peptide displayed thereon; reacting the phage containing the target peptide with a first reagent to derivatize the peptide to form a derivatized peptide, reacting the derivatized peptide with a capture agent comprising a detection marker, thereby incorporating the detection marker within the derivatized peptide; and determining an amount of the detection marker, thereby quantifying the amount of the derivatized peptide displayed on the phage.

The present application provides a highly sensitive method for the quantitative characterization of reaction yields on individual phage clones or for a library of phage. Ideally, the method is suited for the detection of as little as 1 to 100 copies of molecules that have been derivatized by the reactions described herein.

The present method can be employed with known techniques, including detection assays known in the art. Thus, the present method can offer an advantage over prior phage display techniques, which rely on bulk biochemical methods. Further, it has been found that the method of the present invention offers increased sensitivity for detecting derivatized peptides not afforded with prior phage display techniques and assays used to detect displayed peptides.

In certain embodiments, the present method employs the reaction of terminal functional groups on peptides presented on the surface of phage to incorporate detection markers. The detection markers are coupled with chemical moieties to form capture agents. These capture agents react with desired functional groups modified from peptide residues of interest. The detection markers can include, but not limited to, biotin, fluorescein and mannose. Other suitable detection markers known in the art may be used.

The present method provides an improvement over prior methods of phage display because it permits an assay of the yields of the desired phage library or sub-libraries using specific reaction conditions optimized for the particular library or sub-libraries. This is achieved by modifying the functional groups of library members to possess unique properties which are then assayed. These properties can include fluorescence or enzyme-linked quantification. Additionally, the derivative libraries can include macrocycles (which incorporate peptide residues and a light responsive linker) or complex carbohydrate moieties (which cannot typically be incorporated via ribosomal synthesis or enzymatic synthesis), or the method can use multiple reactions for quantitative synthesis of libraries of complex cyclic and poly-cyclic peptides linked by bonds not present in natural peptides. The reactions can then be quantified using standard quantification procedures, to determine the efficiency of production of the phage library.

The present method can be used to generate enriched phage libraries that contain, for example, derivatives that can be synthesized in a sequence of chemical steps from natural peptides. Each derivative, thus, can be easily amplified and characterized. The present method can be optimized for specific reaction conditions depending on the functional group to be assayed.

Phage display, while a robust procedure, is often performed "blindly" with minimal quantitative monitoring during the process. The present method employs the quantification of derivatized phage-displayed peptides to produce optimized reaction conditions to improve the yield of the desired derivatized peptide. Ideally, the method can be used to monitor the success of the phage display earlier on in the reaction process. This reduces the need for bulk biochemical methods which inherently less sensitive, time consuming, and performed often much later in the process.

The present method does not require co-display of any enzymes; the production of synthetic libraries can be done from any phage or viral display. The method can generate a phage that displays chemically modified peptides. Further, there is no need for translational modification within the phage; derivatization of the peptides for detection and quantification occurs on displayed peptides.

In another aspect of the present invention there is provided a method of quantifying an amount of a derivatized peptide displayed on a phage by phage display and comprising an N-terminal serine or threonine residue, the method comprising: providing a phage containing a target peptide thereon; reacting the phage containing the target peptide with a first reagent to derivatize the target peptide, thereby oxidizing the peptide to form a derivatized peptide comprising an aldehyde group, reacting the aldehyde group on the derivatized peptide with a capture agent comprising a detection marker, thereby incorporating the detection marker within the derivatized peptide; and determining an amount of the detection marker, thereby quantifying the amount of the derivatized peptide displayed on the phage.

Another aspect of the present invention is a method for quantification of diverse reactions of aldehydes displayed on peptide or libraries of peptide by monitoring the disappearance of reactive aldehyde group. Reactions described herein are oxime and hydrazine formations, Wittig reaction, cycloadditions with aromatic bis-amines, Dimroth rearrangements. Examples not shown but feasible based on current state of the art include any other reactions of aldehydes or aldehyde-derived imines that take place in aqueous media, such as but not limited to: Morita Baylis Hillman Reaction, Petasis reaction, organocatalytic reactions (asymmetric aldol reactions, Barbas-List Aldol reaction) and metal-catalyzed reactions (aqueous indium-catalyzed allylations, gold-catalyzed alkylation by terminal alkynes).

In accordance with yet another aspect of the present invention there is provided a method of quantifying an amount of a macrocyclic peptide displayed on a phage by phage display, the method comprising: providing a phage containing a target peptide thereon; reacting the phage containing the target peptide with a first reagent to derivatize the target peptide to form a derivatized peptide, reacting the derivatized peptide with $^-C\equiv N^+$-biotin, thereby incorporating the $^-C\equiv N^+$-biotin within the derivatized peptide to form a macrocyclic peptide; and determining an amount of the detection marker, thereby quantifying the amount of the macrocyclic peptide displayed on the phage.

In accordance with yet another aspect of the present invention, there is provided a method of quantifying and selecting a two step reaction sequence, such as cyclization, by incorporating a detection marker in step 1 and elimination of the detection marker in step 2 thereby quantifying and selecting both reaction steps.

In accordance with another aspect of the invention, there is provided a kit for quantifying an amount of a derivatized peptide displayed on a phage by phage display, the kit comprising: a first reagent for reacting with a target peptide displayed on the phage to form a derivatized peptide, and a capture agent comprising a detection marker for incorporating within the derivatized peptide. The kit may also provide a phage library that has been modified chemically or genetically to display a reactive group and can be modified by anyone not trained in the art of bioconjugation by one-step mixing with reactive agent. The kit can provide a capture reagent that can assess the amount of reactive group before and after modification, thereby providing a simple and accurate measure of the yield of the modification. In one kit, the library is already reactive and does not require activation; the capture agent allows the user to assess both quality of library (i.e. amount of reactive groups) and extent of modification (i.e. amount of reaction groups left after modification). For example, this can include bioconjugation to a specific reactive group already present on phage (e.g., phage has aldehyde and user simply modifies it without concern about formation of such aldehyde). Another kit in accordance with the present invention can be used to perform and quantify any activation (e.g. oxidize the phage to aldehyde and then react the aldehyde).

BRIEF DESCRIPTION OF THE FIGURES

For a better understanding of the present invention, as well as other aspects and further features thereof, reference is made to the following description which is to be used in conjunction with the accompanying drawings, where.

DETAILED DESCRIPTION

Definitions

Figure 1:
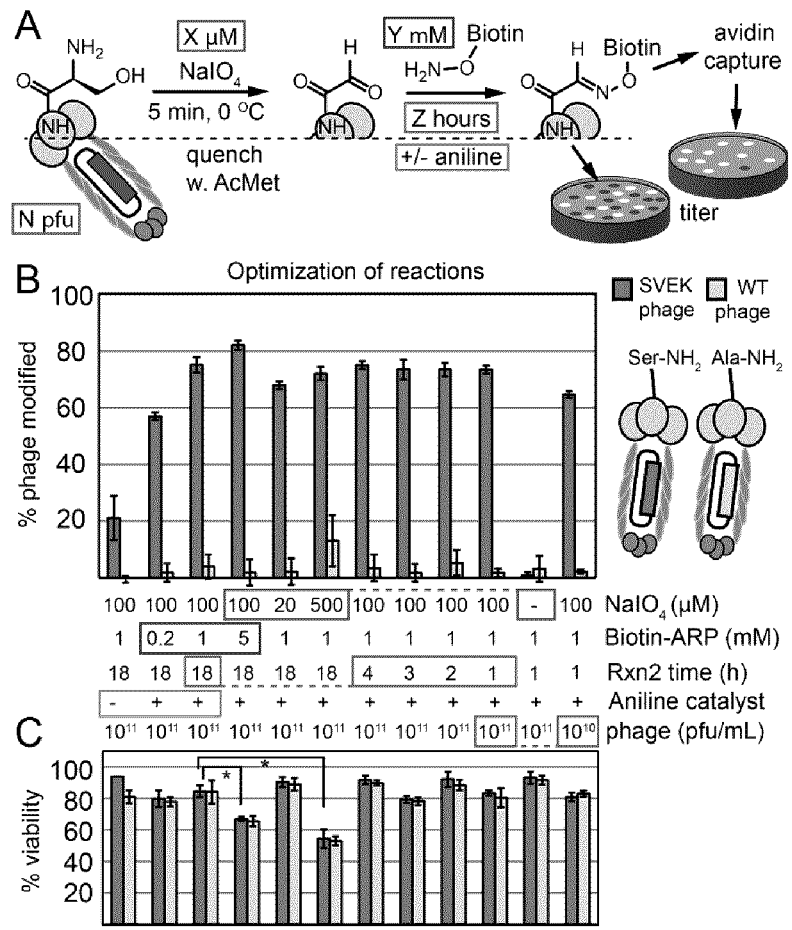
FIG. 1 shows an example of optimization and quantification of chemical reactions on phage during oxidation of the N-terminal amino acids displayed on phage.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

The term "assay" is used herein to refer to a test to qualitatively or quantitatively detect the presence of a substance in a sample.

The term "biological sample" is used herein to refer to both animal and human body fluids, excreta and tissues obtained from a living or dead organism. The term "body fluid", as used herein includes a naturally occurring and/or secreted and/or excreted and/or discharged fluid and/or wash fluid from the surface or inside the bodies of a human or an animal and includes, but is not limited to: saliva, sputum, serum, plasma, blood, pharyngeal, nasal/nasal pharyngeal and sinus secretions, urine, mucous, feces, chyme, vomit, gastric juices, pancreatic juices, semen/sperm, cerebral spinal fluid, products of lactation or menstruation, egg yolk, amniotic fluid, aqueous humour, vitreous humour, cervical secretions, vaginal fluid/secretions, bone marrow aspirates, pleural fluid, sweat, pus, tears, lymph and bronchial or lung lavage.

The terms "body tissue" or "tissue", as used herein, refer to an aggregate of cells usually of a particular kind together with their intercellular substance that form one of the structural materials of a plant or an animal and that in animals include, for example, connective tissue, epithelium, mucosal membrane, muscle tissue, placental tissue, and tissue from liver, intestines, spleen, kidney, brain, heart, nerve tissue, and the like. Samples of body tissue can be obtained from living humans or animals by a variety of non-limiting methods, such as fine needle aspirates, scrapings or biopsy tissue or from the remains of dead humans or animals. The term "tissue" can be used to refer to naturally occurring tissue or synthetic tissue.

Biological samples can also include pre-processed foodstuffs including plants, samples of meats and processed foods, as well as swab samples from environmental sources such as food processing facilities, hospitals, water, soil, and air. Other biological sample types include isolates/fractions/concentrates of blood (e.g. platelets, red blood cells, white blood cells or leukocytes), including umbilical cord blood or placental blood, bone marrow, aspirates, fine needle organ or lesion aspirates, cervical samples, cultured cells, body swabs, or body smears.

The terms "dormant bacteriophage" and "dormant phage" are used interchangeably to refer to bacteriophage that is non-infective, but that will become infective following activation.

As used herein, the term "reporter gene" refers to a construct comprising a coding sequence attached to heterologous promoter or enhancer elements and whose expression product can be assayed easily and quantifiably when the construct is introduced into bacteria, for example through infection by bacteriophage carrying the reporter gene.

As used herein, a "target peptide" is a peptide of interest displayed on the surface of phage that is to be derivatized and assayed. As would be understood, the surface of a phage can display a plurality of peptides; a target peptide, thus, is one of the plurality of displayed peptides which is targeted for derivatization and assaying.

The term "capture agent" as used herein refers to a compound that reacts with a particular functional group on a phage-displayed peptide. The capture agent comprises a reactive moiety that reacts with the desired functional group, and a detection marker which is used to quantify the binding of the capture agent with the peptide. "Detection marker", thus, refers to a molecule in association with the moiety to form the capture agent, and that is capable of being assayed when the capture agent reacts with and is attached to the desired functional group. Exemplary capture agents include those comprising reactive moieties that react with terminal aldehyde groups on the phage-displayed peptides, for example. Exemplary detection markers include biotin, fluorescein and mannose.

As used herein, "derivatization" in the context of a "derivatized phage molecule" or "derivatized peptide" refers to the modification of a target peptide residue presented on the surface of a phage, prior to reaction with a capture agent. The modification typically involves reaction of a particular functional group presented on the target peptide, such as the terminal peptide residue, thus forming a derivatized phage molecule, such as a derivatized peptide. This derivatized peptide is then detected by and reacted with the capture agent.

Phage Display Quantification Process

The quantification process as described herein generally employs two types of phage: peptide-displaying phage "P" and control peptide-free phage "C". P contains an insert in its genome which encodes and displays a peptide with its coat proteins. P can also represent a library of sequences ($P_{lib}$). The present method is designed such that no change in procedure is necessary when characterizing reaction on one phage P or a library of phage $P_{lib}$.

The control phage C is typically genetically similar to P, but lacks inserts in the phage genome and, thus, a lack of DNA sequence encoding peptides in the coat protein region. It is desired to be able to perform independent quantification of number of P and C phage particles in the same solution.

Methods known in the art can be used to differentiate P and C phages. For example:

i) P containing LacZ, while C is LacZ-free. The plaques corresponding to P and C are distinguishable by color on plates containing colorimetric reagent X-gal. Any suitable enzyme other than LacZ can be used, and visualized using known means, such as with a fluorescence substrate.

ii) P containing genes encoding GFP, RFP or other fluorescent reporters in the genome, while C is reporter-free. The reporter does not have to be physically linked to any proteins of the phage; it simply can only be expressed in the host cell. The plaques corresponding to P and C can be distinguished by color or fluorescence on plates as described previously.

iii) P containing antibiotic resistance gene in the phage genome, while C is resistance-free. The plaques corresponding to P and C can be distinguished by plating the mixture of phage on two plates, with and without the antibiotic. Alternatively, P and C can carry resistance for two types of antibiotics and visualized separately.

iv) P comprises a sequence encoding a short peptide sequence such as FLAG recognized by a specific ligand, such as anti-FLAG antibody, while C is sequence-free. P and C phage can be distinguished by transferring the colonies onto nitrocellulose paper and probing with the antibody or other ligand.

v) A mixture of P and C can be lysed to isolate DNA and subject to quantification of specific DNA sequence by real-time PCR or other quantitative methods. Primers for PCR are designed for insert region would recognize DNA of only P but not C.

The characterization of the mixture of P and C is beneficial for determining the success of the phage display process. Alternatively, P and C can be modified chemically and quantified in two separate solutions. For simplicity, in all subsequent discussions, examples of the present method as described herein are based on the presence of reporter Xgal in P but not in C. This method allows for rapid quantification of P and C by counting plaques of specific color (blue for P and white for C) in a plaque-forming assay.

Analysis and Quantification of Phage Displayed Peptide Derivatives

Characterization of phage libraries can be a challenge, because each library member is often present in mixture as a single molecule (single clone). The present method allows for quantification of reaction yields in multi-step reactions on complex mixtures of clones (for example, up to $10^9$ different peptides) using a series of capture agents for each reaction step. The method as described herein employs any known substrate molecule and detection technology that can be conducted on amino-acid sequences.

Quantification and characterization of the chemical reactions in peptide libraries has been lacking. Existing approaches for quantitative characterization by spectroscopic methods (mass-spectrometry, elemental analysis) and biochemical methods (gel electrophoresis, Western blot, etc) are typically only applicable to large clonal population or phage and viruses (e.g., $10^{10}$-$10^{13}$ particles). They cannot detect modifications which occur in a population that contains millions of different phage clones, with each clone present in low amount (e.g., 1-100 copies). The present method provides optimized reaction conditions for assaying derivatized peptide libraries.

The present method can also be used for the improvement of yield in chemical reactions conducted on derivatized peptide libraries. In a collection of many peptides, certain peptides undergo a specific type of the reaction faster than others. For example, cyclization can occur faster in peptides of specific conformation, while substitution or elimination can occur in peptides of specific steric and electronic properties. Although the selection of individual peptide sequences with unique reactivity has been described previously (Barbas, et al., U.S. patent application Ser. No. 08/573,415, filed Dec. 15, 1995; Eldridge, G. M., Weiss, G. A. (2011), Hydrazide reactive peptide tags for site-specific protein labeling. *Bioconjugate Chem.* 22: 2143-2153), the present invention allows for the optimization of multi-step reactions on peptides to generate a large library ($10^3$-$10^8$) of non-peptidic structures in high yield. Although these libraries are non-peptidic in nature, they are amplifiable quantitatively just like parent peptides. Their identities are genetically-encoded and can be deduced from the original peptidic starting materials.

One advantage of the present method is serial optimization of the two-step modification of phage libraries. In one example, quantification of oxidation of N-terminal serine (Ser) and threonine (Thr) electrophilic addition to aldehyde is performed. In another example, quantification of site-selective reduction or disulphide and its alkylation by light-sensitive linker is shown. However, it would be understood that other functional groups, on other amino acids, whether terminal or internal within the displayed peptide, may be contemplated. The examples shown herein illustrate only certain embodiments of the present method.

A library of phage-displayed peptide-derivatives generated with the help of a quantification approach contains a well-defined number of ligands of defined structure. In standard phage display, rounds of panning and amplification discover new peptides; in a library of peptide-derivatives rounds of modification, panning and amplification discover new peptide-derivatives.

To illustrate the above described system and method, an exemplary panning of peptide-derivatives is shown on model proteins targets, such as streptavidin (for binding to biotin) and Concanavalin A (for binding to mannose). However, as would be readily understood that other protein targets using other capture agents and detection markers can be used.

The phage concentrations $[P]_0$, $[C]_0$, $[P]_{b4}$, $[C]_{b4}$, $[P]_{af}$ and $[C]_{af}$ measured in the present method provide information about yield and specificity of the reaction (initial step 1), as well as its interference with viability of phage. Serial variation of the reaction conditions can be then performed to identify the best outcome in those parameters.

The present method can be applied to other multi-step reactions. For example, multi-step reactions (Rxn1, Rxn2, etc.) can employ different reaction conditions. Rxn2 converts functional group F1 from Rxn1 to another functional group F2. To characterize Rxn2, a mixture of phage from reaction 1 is exposed to appropriate reagents (Reag2.1 Reag 2.2, etc). After an appropriate time, the reaction is terminated and the yield concentration of group F2 is determined using capture agent 2 (CA2), which contains a group reactive with F2. Exposure to capture agent CA1, reactive to original group F1, can be used to quantify the amount of unreacted groups F1. For example, quantification of the reaction of aldehyde with hydroxylamine can be done by counting phage with unreacted aldehyde groups, using aldehyde reactive capture agent. Further, quantification of the reaction of thiols (quantification of unreacted thiols) can be done using thiol-specific capture agent. Also, quantification of the cyclization can be done using chloroacetamide reactive capture agent. Examples of these reactions are described herein.

Thus, quantification and optimization of a N-step reaction can be done using N capture agents to quantify the yield at each step. Changing the condition at each step optimizes the yield at each step.

The capture agents (CA1, CA2, etc., described above for quantification) can serve another purpose. They can be used to select members of the library that are prone to undergo a particular reaction more effectively. This selection can be applied when reactions are conducted on mixture of phage that display library of peptides $P^{lib}$. By running reaction on $P^{lib}$ and C in specific conditions, the yield can be quantified using capture agent CA1. Unreacted peptides can be separated from those that are reacted. A sub-library containing derivatized peptides can be amplified to give a pure sub-population of phage that contain modified ligands only. The present method provides several examples of this, including: (1) modification of a random library to select a sub-library with N-amino acids reactive to oxidation; and (2) modification of a random library of 7 amino acids flanked by two cysteines to select sub-library that can undergo efficient cyclization with unnatural linker.

Calculations of Yield and Viability

Yield of the specific reaction is determined as:

$$Y^s=100\%*[P]_{af}/[P]_{b4}$$

Yield of the non-specific reaction is determined as:

$$Y^n=100\%*[C]_{af}/[C]_{b4}.$$

Yield of the reaction that occurs specifically on a peptide, as opposed to any other protein segment of the phage, is determined by comparing $Y^s$ and $Y^n$. Ideally, the $Y^n$ is zero, while $Y^s$ is close to 100%.

Figure 3:
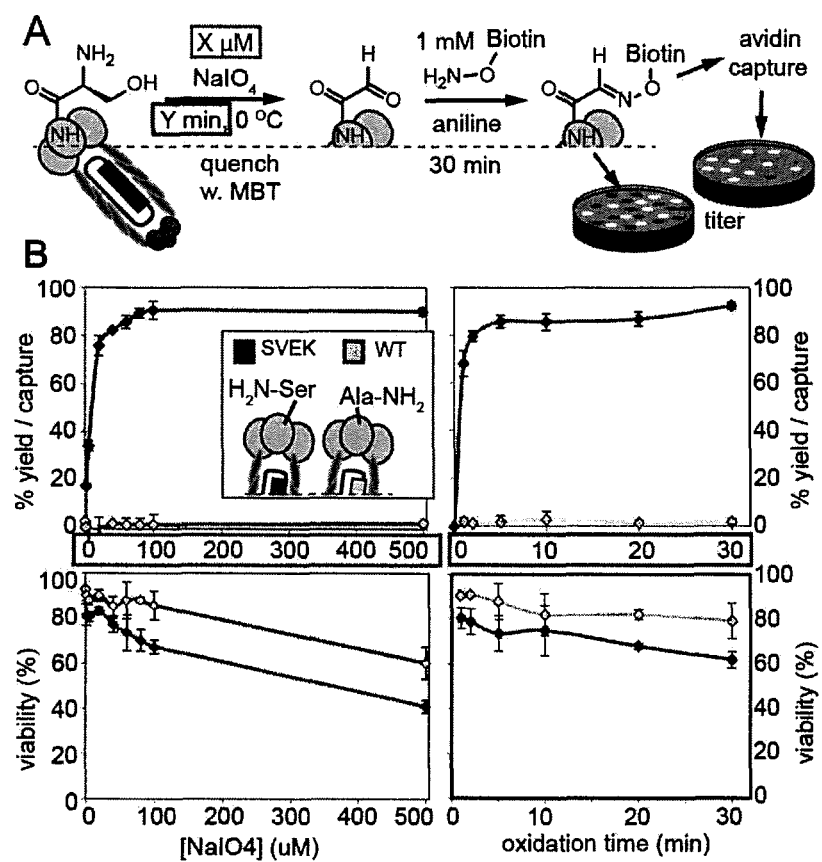
FIG. 3 shows an assessment of the kinetics of the oxidation of the N-terminal Ser on phage.

The viability of the phage over the course of the reaction is determined as $V=100\%*[P]_{b4}/[P]_0$. Ideally, the viability of the reaction should be maintained close to 100%, and optimization of the length of reaction, and concentration of reagents, or their presentation can be used to maximize V. This can result in an increase of the yield with a decrease in viability, as shown herein (see, for example, in FIGS. 1 and 3).

The ability to quantify the yield allows for rapid selection of optimal reaction conditions, which maximizes yield and specificity and minimizes interference with viability. Parameters that can be varied to optimize the yield and specificity include: reagent concentration and reaction time, and the presence of a catalyst. These parameters are exemplified herein.

To gain a better understanding of the invention described herein, the following examples are set forth. It should be understood that these examples are for illustrative purposes only. Therefore, they should not limit the scope of this invention in any way.

EXAMPLES

Example 1: Two-Step Modification of Phage Libraries

The synthesis of peptide derivatives is a sequence of reactions (for example, labelled "Rxn1", "Rxn2", etc.). In reaction 1, a mixture of peptide-displaying phage [P] and control peptide-free phage [C] in known concentration $[P]_0$ and $[C]_0$ are mixed with appropriate reagents ("Reag1.1", "Reag1.2", etc). After an appropriate time, the reaction is terminated and a capture agent 1 (CA1) is added. The capture agent typically contains a complimentary reactive group and, for example, biotin. The solution is then mixed with capture support (such as a magnetic bead with a biotin-binding protein streptavidin). Phage that has undergone the Rxn1 successfully is captured on the support. The numbers of phage before capture ($[P]_{b4}$ and $[C]_{b4}$) and after capture ($[P]_{af}$ and $[C]_{af}$) are recorded.

FIG. 1 shows optimization and quantification of chemical reactions on phage during oxidation of the N-terminal amino acids displayed on phage. In FIG. 1 Rxn1 comprises the oxidation of an N-terminal serine residue by Reag1.1=$NaIO_4$, which produces an aldehyde moiety. Capture agent CA1 is aldehyde-reactive biotin-hydroxylamine. A phage or library of phage that presents peptide with N-terminal Ser or Thr can be oxidized to aldehyde. The amount of the aldehyde and specificity of the oxidation can be assessed using an aldehyde-reactive capture agent (2). A phage is then captured using streptavidin-coated magnetic beads. Quantification of the number of phage before and after capture can be used to calculate the yield of the reaction. The concentration of reagents and timing of reactions was used to maximize the yield.

FIG. 1B illustrates a profile of the yield and specificity of the reaction in different reaction conditions. Reactions were performed on mixture of phage clones: (1) phage displaying a peptide with N-terminal Ser ("SVEK phage") and (2) phage containing N-terminal Ala ("WT"). Two phage clones were characterized independently because SVEK contained LacZ reporter and formed blue plaques, while WT formed white plaques. Identical characterization can be performed using a library of clones that contain N-terminal Ser.

FIG. 1C illustrates a profile of the viability of the phage in individual reaction conditions. The method can be used to rapidly profile multiple conditions to select those that maximize the yield of specific reaction on SVEK phage, minimizes non-specific reaction on WT phage, minimizes reaction time, and maximizes the viability of the phage (see boxed values). As demonstrated herein, the ideal concentration of $NaIO_4$ in Rxn1 is 20-500 µM, more particularly 20 µM or 500 µM.

The concentration of biotin-ARP was also optimized to avoid non-specific binding. Ideally, the concentration of biotin-ARP is about 0.2-5 mM, typically 0.2 mM, 1 mM or 5 mM. The ideal reaction time (Rxn 2) was found to be 1-4 hours, typically 1, 2, 3 or 4 hours incubation time. The addition of an analine catalyst was found to favourably promote the reactions.

Figure 2:
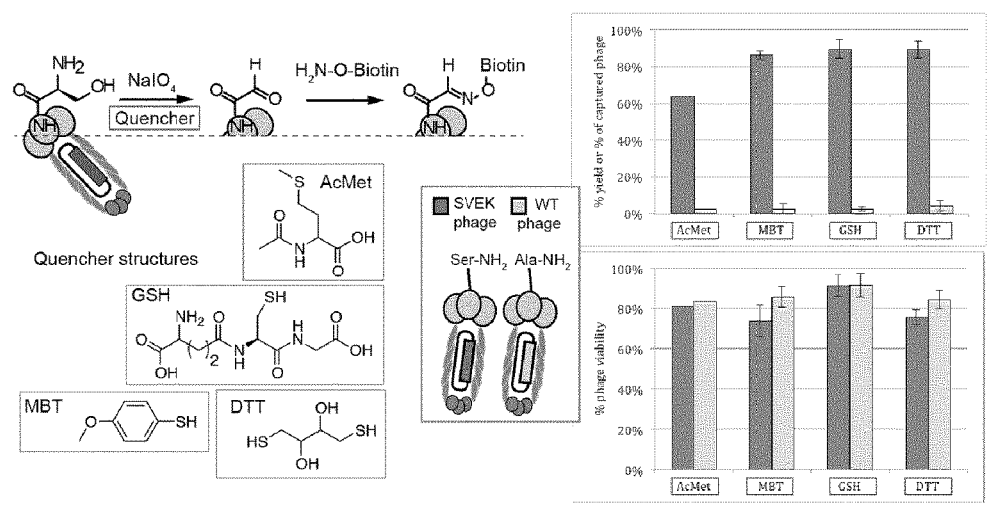
FIG. 2 shows profiles of the effect of oxidation-quencher on reaction efficiency.

FIG. 2 shows a profile of the effect of an oxidation-quencher on reaction efficiency. The oxidation of N-terminal Ser on phage can be terminated by a variety of reducing agents. The use of some reducing agents (thio vs. sulfide) can dramatically improve the yield. Thiol-based reducing agents provide similar yields, but glutathione has the least negative impact on phage viability.

In FIG. 3A, the oxidation of N-terminal Ser presented on phage was "fine tuned" to produce an optimal yield of captured phage. All reactions were conducted with $10^{11}$ pfu/mL of phage. After each oxidation, the reaction was terminated with 4-methoxybenzenethiol; the phage was exposed to 1 mM biotin-hydroxylamine for 1 h, diluted 1,000,000-fold and captured on Strep-MB. The resultant kinetic curves (FIG. 3B) demonstrate that yield of the reaction in these conditions cannot be increased beyond 90% regardless of oxidant concentration or reaction time (top two panels). At extended reaction time or high oxidant concentrations, a decrease in viability take place (lower panels). Side reactions, including modification of WT phage, are minimal in these reaction regimes.

Figure 4:
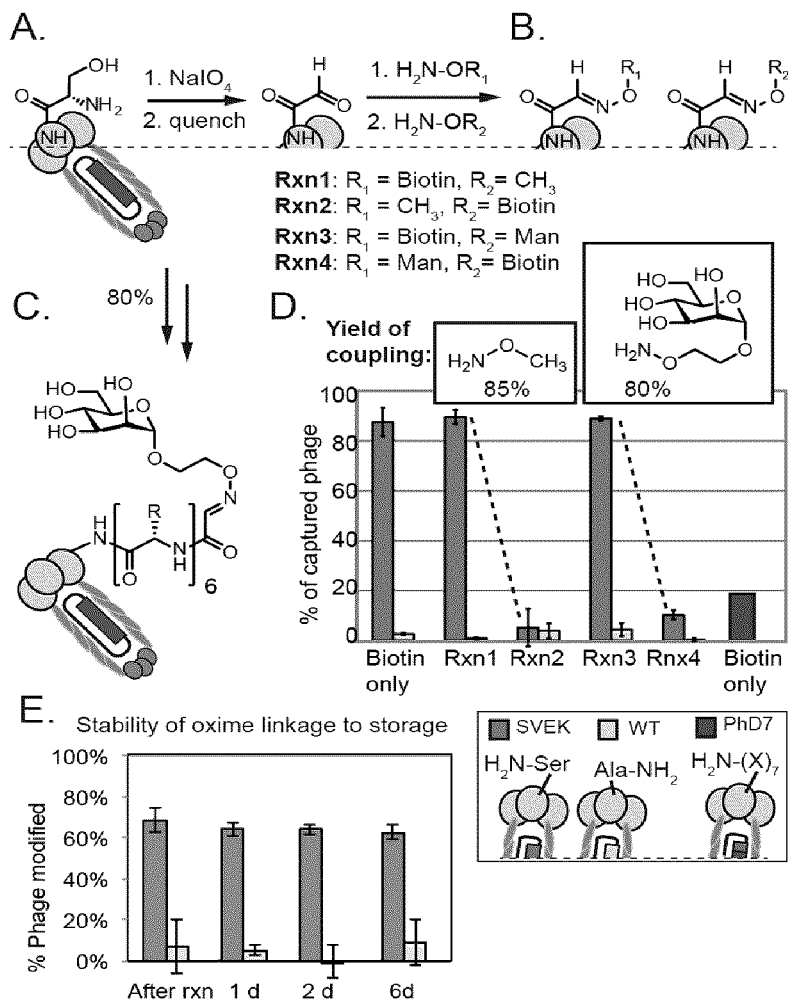
FIG. 4 shows exemplary yields of oxidation to aldehyde and oxime formation.

FIG. 4 shows a profile of the yield of a two-step reaction: oxidation to aldehyde and oxime formation, by characterizing unreacted aldehydes. In panel A, phage was exposed to optimal oxidation conditions (0.06 mM $NaIO_4$ for 5 min) and quenched with glutathione. The phage was then exposed to mannose-hydroxylamine. The amount of unreacted aldehydes were quantified by exposure to capture agent biotin-hydroxylamine (panel B). As illustrated in the graph therein, approximately 90% of the phage is reactive towards biotin-hydroxylamine, but only 10% of phage are modifiable by biotin-hydroxylamine after 1 h exposure to 1 mM mannose-hydroxylamine. This yield of reaction with mannose-hydroxylamine is 90–10=80% (Panel C). Panel D shows that 20% of the phage in a random library is reactive towards biotin-hydroxylamine after oxidation, confirming that 20% of the library contain N-terminal Ser or Thr residues. Panel E illustrates that the chemical bond on phage is stable for multiple days.

Figure 5:
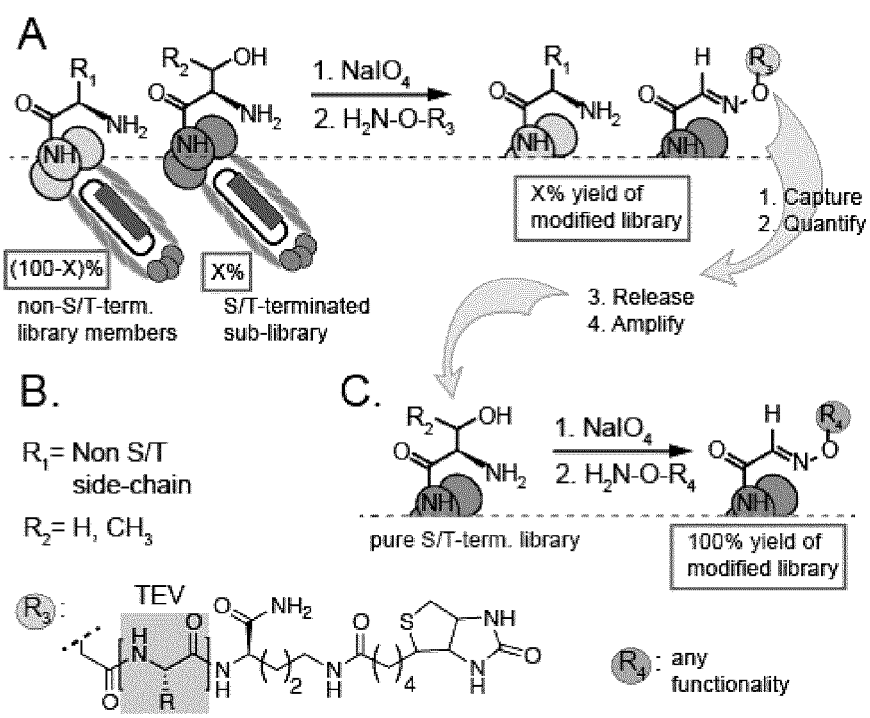
FIG. 5 shows a schematic for selecting the subset of a library reactive in oxidation and coupling.

FIG. 5 A to C illustrates a method of selecting a subset of a library reactive in oxidation and coupling to determine the yield of displayed peptides comprising terminal Ser/Thr residues ("SIT-terminated sub-library") vs. library members not containing terminal Ser/Thr residues ("non-S/T-term. Library members"). In this example, a random library of phage (panel A) was exposed to optimal oxidation conditions (0.06 mM $NaIO_4$ for 5 min) and quenched with glutathione and oxime-formation conditions (1 mM biotin-TEV-hydroxylamine). Since only 20% of the random library contains N-terminal Ser, the yield of the reaction on random naive library is ~20%. After release of the captured phage, and re-amplification (panel C), the yield of identical reaction in identical conditions is typically higher, approaching nearly 100% yield after a few rounds of this selection. This process, thus, selects a subset of library that reacts optimally in these reaction conditions.

Figure 7:
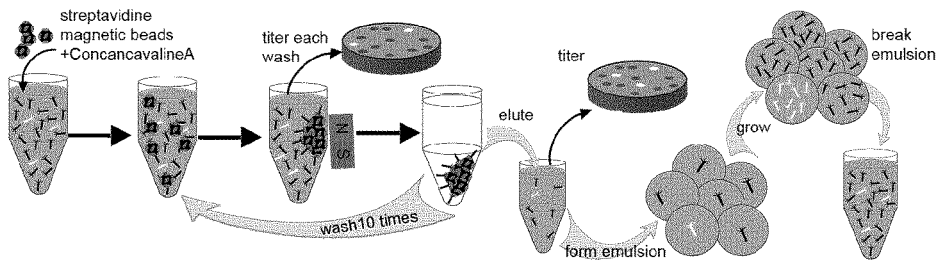
FIG. 7 illustrates kinetics of panning and amplification of peptide derivatives synthesized via oxidation-oxime ligation.
Figure 7:
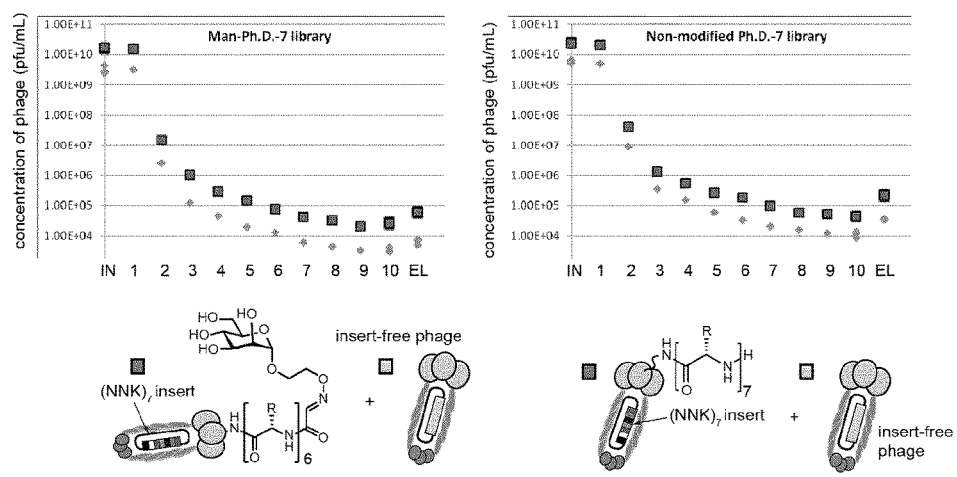

FIG. 7 shows that a library of peptide derivatives synthesized via oxidation-oxime ligation can be used in panning and amplification. Example of panning of peptide-Mannose conjugates against a model mannose-binding target, Concanavalin A, and panning of the peptide library which has not been modified are shown. To assess the efficiency of panning, the amount of phage washed at each step was measured. From these values and the amount of phage eluted from beads, back-calculation of the amount of phage on-bead at each washing step determined the quantity of phage. These values follow standard first-rate off-rate kinetics. Each library has been deliberately contaminated with insert-free wild type phage, which can be quantified in the mixture, because it forms plaques of white color. By contrast, the library forms plaques of blue color. Insert-free phage serves as internal control for non-specific binding. To assess the efficiency of panning, the amount of "blue" and "white" phage washed at each step was measured. An increased number of phage at the elution step (EL) as compared to the last washing step (wash 10) indicated that the phage was recovered due to non-specific interaction. For more details about blue-white screen in phage-display panning see: R Derda, S Musah, B P Orner, J R Klim, L Li, L L Kiessling "High-throughput Discovery of Synthetic Surfaces that Support Proliferation of Pluripotent Cells" *J. Am. Chem. Soc.* 2010, 132, 1289.

Example 2: Optimization of Cysteine (Cys)-Containing Residues

Figure 8:
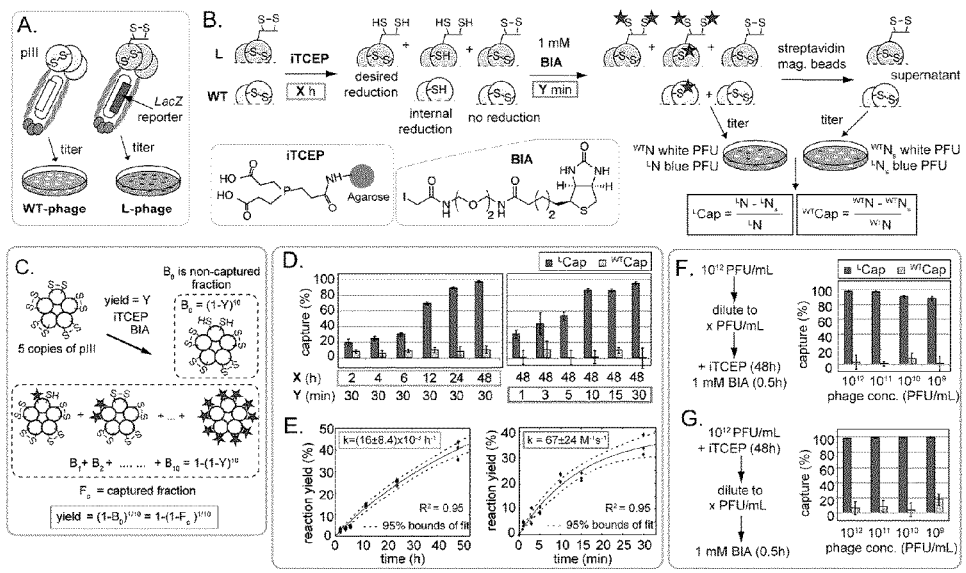
FIG. 8 illustrates a reaction showing optimization of the synthesis of peptide derviatives via reduction of disulfides and alkylation of cysteines.

FIG. 8 illustrates the optimization of synthesis of peptide derivatives via reduction and alkylation of phage displayed peptides. (A) Reactions were performed with a mixture of L-phage that displays disulfide CPARSPLEC and forms blue plaques with WT-phage that displays no peptide and forms white plaques. (B) After exposure of WT+L mixture to iTCEP and BIA, white and blue plaques after reaction ($^{WT}N$ and $^{L}N$) and after the biotinylated phage is captured by streptavidin ($^{WT}N_s$ and $^{L}N_s$) was counted. Capture of L phage ($^{L}Cap$) was used as measure of biotinylation. Capture of WT phage ($^{WT}Cap$) typically indicates non-specific reduction or alkylation; however, significant capture was not observed (see D-G). (C) Biotinylation of five pIII-displayed disulfides yields phage with 0-10 biotins ($B_0$-$\alpha_{10}$) is shown. Reaction yield is calculated from captured fraction. (D) After exposure of WT+L mixture to iTCEP and BIA, capture of L-phage increases with the time of reduction and alkylation. (E) Captures were converted to yields using equation (C) and the data were fit to pseudo-first order kinetics. This kinetics was appropriate because [iTCEP] and [BIA]>> [phage] and the yields of reduction (F) and alkylation (G) of phage at a specific time were independent of the concentration of phage.

Figure 9:
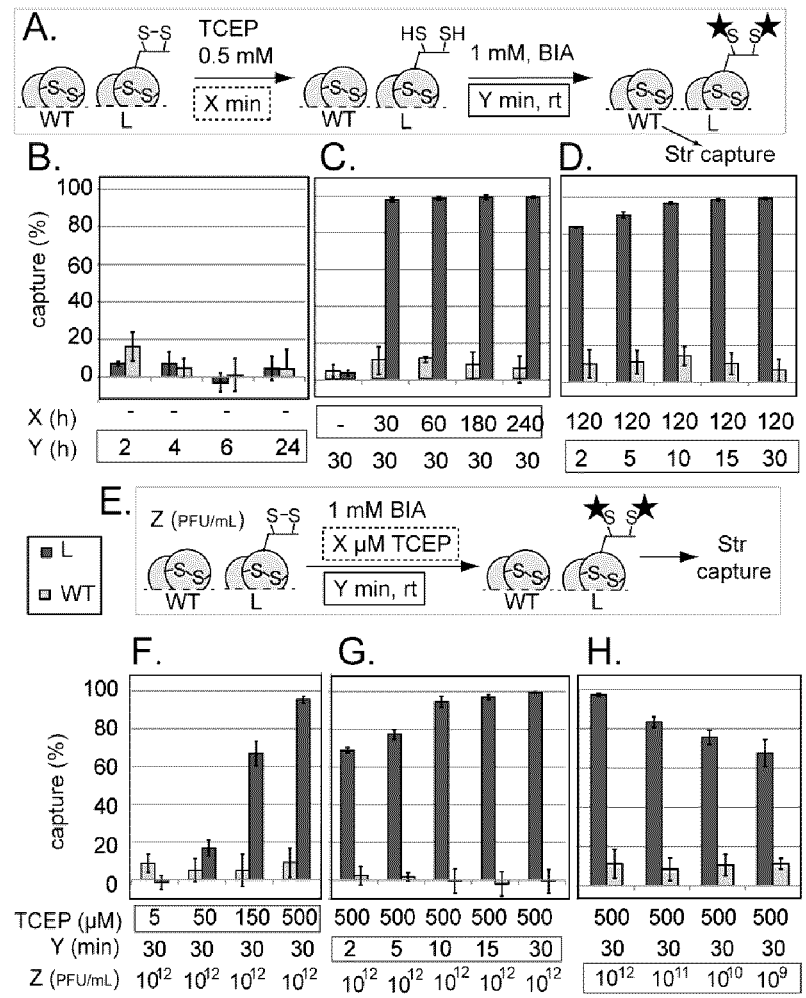
FIG. 9 illustrates schematics and results from analysis of kinetics of reduction and alkylation.

FIG. 9 shows one embodiment of tuning the kinetics of reduction and alkylation of the disulfide residues on Cys by TCEP and their subsequent alkylation by BIA. A) Alkylation of phage does not occur in the absence of reducing agent. Panel B illustrates quantification of yield of alkylation of phage clone L by BIA after reduction by TCEP. Panel C indicates reduction by TCEP is complete in <30 minutes. The total reaction time is X min. Panel D indicates optimization of alkylation time after 2 h reduction of phage. The total reaction time is X+Y min. Panel E illustrates optimization of one-pot reduction/alkylation of phage by varying (F) concentration of TCEP and (G) reduction time. As shown in Panel H, efficiency of one-pot reaction drops to 60% when phage concentration is <$10^9$ PFU/mL due to low TCEP reduction efficiency at these concentrations.

Figure 10:
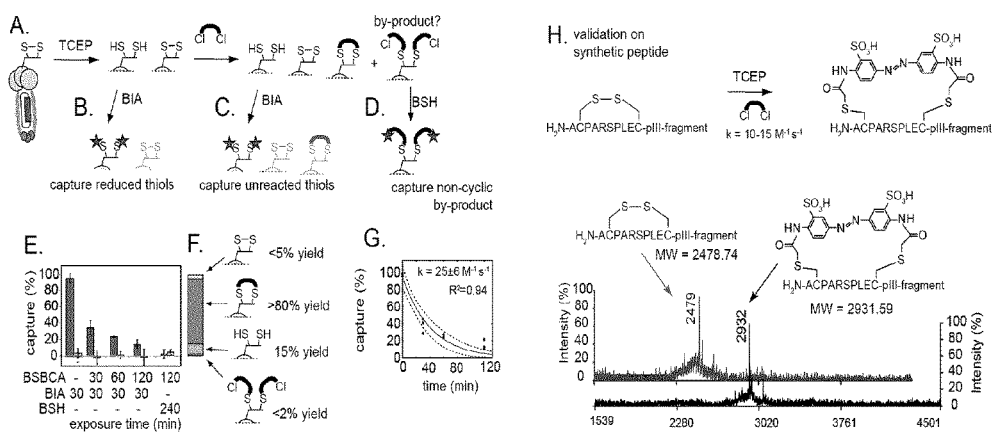
FIG. 10 shows a scheme and results of optimization of the linker coupling and a cyclization reaction on clonal phage.

FIG. 10 illustrates one example of optimization of the linker coupling and cyclization on clonal phage and library phage. In panel A, reduction and alkylation of the disulfide peptide displayed on the phage and potential resulting by-products is shown. Exposure to (B) BIA is used to quantify the reduced disulfides or (C) unreacted thiols. Panel D illustrates that exposure to biotin-thiol (BSH) quantified non-cyclized peptides. In Panel E, the fraction of biotinylated phage decreases after incubation of phage with BSBCA. No biotinylation after exposure to BSH indicated that BSBCA coupling yielded cyclic peptide as major product. In Panel F, disappearance of biotinylated phage was fit with pseudo-first order kinetics to calculate the rate constant (k) of alkylation by BSBCA. In Panel G, two rate constants measured for two phage-displayed peptides (F1, F2) were similar to those measured using HPLC and a synthetic peptide of the same amino acid sequence (P1, P2). As shown in Panel H, mass spectrometry confirmed that a cyclic product was major product of reaction between BSBCA and peptide ACPARSPLEC<u>GGGSAETVESC(Cam)LAKS</u> (underlined sequences is a synthetic fragment of pIII).

Example 3: Cyclization Reaction

Exemplified herein is the generation of large sub-libraries, from random peptide libraries, that undergo quantitative N-terminal oxidation, and an efficient three-step cyclization via nucleophilic substitution, cyclization and rearrangement through the Ugi reaction.

A selection for sub-library of sequences that can undergo complex, multi-component reactions involving multiple natural side chains. As an example, the Ugi multi-component reaction was performed. This reaction requires amine, carboxylic acid, aldehyde and isocyanide (see FIG. 6). Components in the phage library can be oxidized at the N-terminus (Ser and Thr-terminated peptides). Only some sequences can undergo efficient cyclization. Using an isocyanide with a capture agent (such as biotin), sequences that undergo efficient cyclization can be separated from those that do not. The sub-library can be used to generate a pure library of phage-displayed macrocycles.

Figure 6:
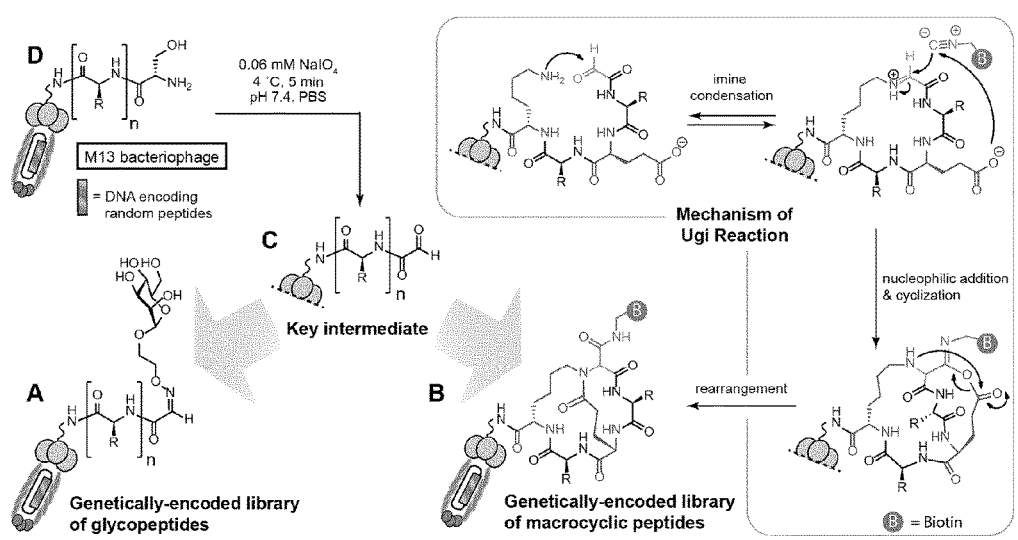
FIG. 6 illustrates the synthesis of genetically-encoded chemical libraries of glycopeptides (A) or macrocyclic peptides (B).

FIG. 6 illustrates one example of selecting for genetically-encoded chemical libraries of glycopeptides (A) or macrocyclic peptides (B). These peptides are derived from aldehyde-containing peptides (D, and intermediate C). The aldehyde displaying libraries can be quantitatively produced from any native phage-displayed peptide library; the yield of this reaction can be maximized as described in FIG. 5. A key aldehyde intermediate (C) leads to different libraries in a one-step synthesis. The Ugi reaction is shown: addition of $^-C\equiv N^+$-biotin initiates a cascade of cyclization and rearrangement to afford the complex macrocyclic peptides. Only product that undergoes complete transformation incorporates biotin within it. A sub-library, which undergoes Ugi macrocyclization, can thus be isolated and re-amplified to yield a pure, genetically encoded library of macrocycles.

Figure 11:
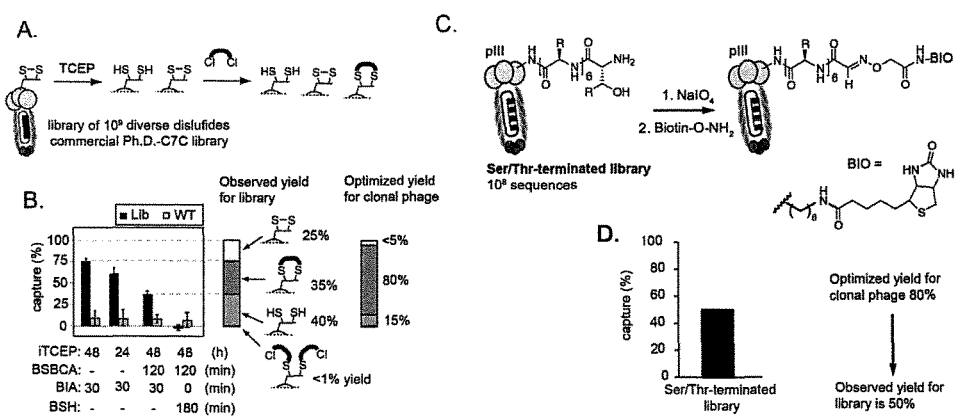
FIG. 11 shows a scheme for optimization of a cyclization reactions on library phage and differences in reactivity between clonal population of phage and library of phage.

FIG. 11 illustrates one exemplary scheme for the optimization of library on phage. Conditions that are optimal for phage that display individual sequences do not yield the same yields on libraries containing multiple reactive peptides. Panel A illustrates one scheme of the reduction and alkylation reactions. In Panel B, the observed yield of the alkylation in the library is ~35%—same conditions for clonal population of phage yield >80% alkylated phage (FIG. 10). In Panel C, the expected coupling in oxime modification, based on optimized conditions for clonal population of phage (FIGS. 2 and 3) is ~80%. The observed yield in the library is 50% (Panel D). Thus, it has been surprisingly found that conditions optimized for clones that display one type of peptide provide much lower yield in large libraries of clones presenting diverse peptides. Differences depend on the specific reaction and vary from subtle differences 80% (clone) in 60% in library to significant variations >99% (clone) in 50% (library).

Figure 12:
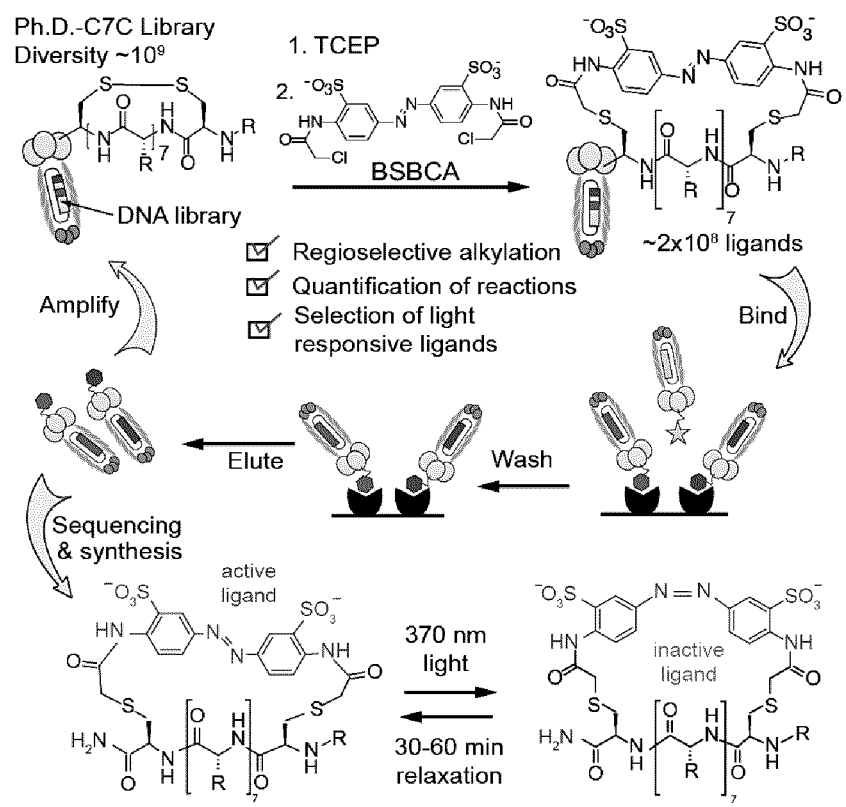
FIG. 12 illustrates a scheme for the generation of a light responsive library using cyclization with a light responsive linker.

FIG. 12 shows an example of the selection of chemically modified genetically-encoded library and general strategy for the synthesis of genetically-encoded light-responsive phage libraries. The yield of each step (reduction, alkylation, cyclization) can be improved using steps described herein (FIGS. 7-9) to yield a pure library, in which every member contains light responsive linker.

Figure 13:
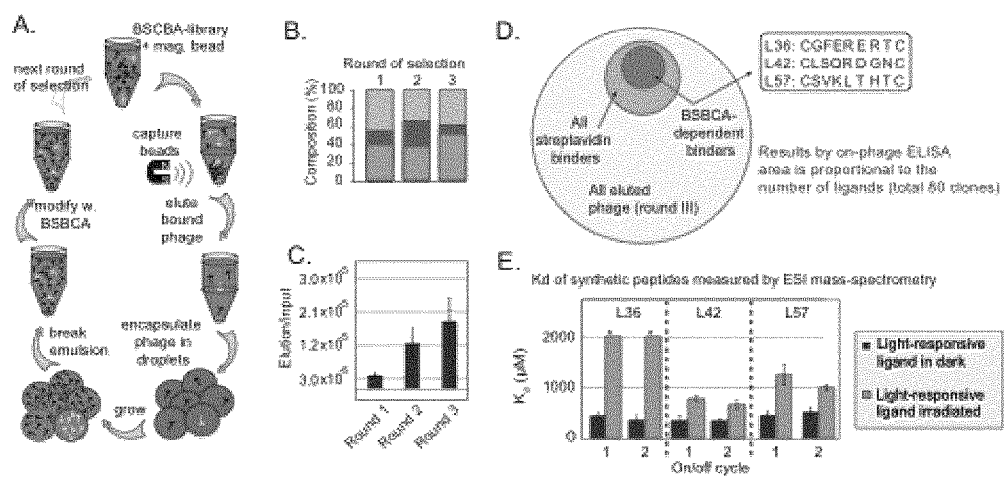
FIG. 13 illustrates results of panning a library cyclized with unnatural light-sensitive linker.

FIG. 13 shows the results of panning of a library cyclized with an unnatural light-sensitive linker. In Panel A, a scheme of panning procedure for modified library against streptavidin is shown. In Panel B, stacked bars show composition of the library before each round of the panning. Panel C shows enrichment of binding ligands after each round of panning represented as the ratio of the number of eluted bound phage to the number of phage input at each round. Panel D shows a Venn diagram representation of phage population after panning. Area is proportional to the number of binding/non-binding phage clones; data based on ELISA screening of 80 clones. As shown in Panel E, iterative irradiation of L36 and L42 did not cause a significant change in photo-switching ability of the ligands. The * shows that no complex was observed. The Ugi reaction is just one example of a modified sub-library that can be made. Other reactions may be used as applicable involving aldehyde, such as Passerini reaction, Petasis reaction, Wittig reaction, or Mukaiyama aldol reaction.

Example 4: Comparison of Present Method with Other Biochemical Methods

Figure 14:
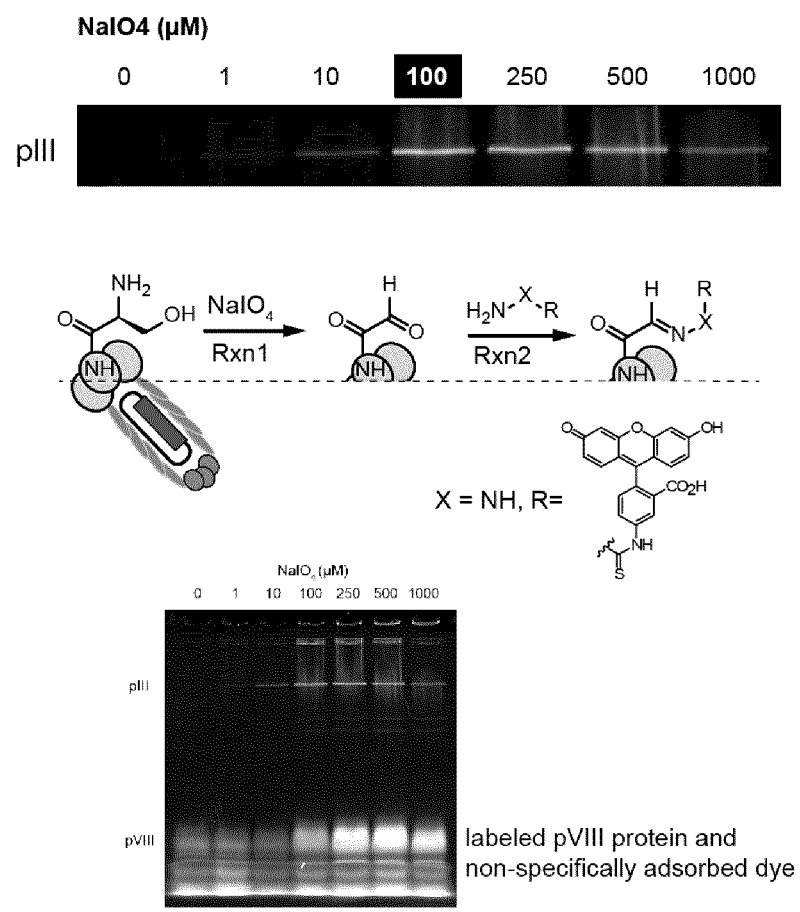
FIG. 14 illustrates the quantification of reactions, described in FIG. 1-7, using other biochemical methods.

FIG. 14 illustrates the quantification of reactions, described in FIG. 1-7, using other biochemical methods. The coupling of fluorescein was used to visualize which protein of phage the reaction occurs on. The bands of the SDS page gel, which correspond to minor protein pIII become progressively more fluorescent with increasing concentration of fluorophore (using semi-quantitative analysis). Because pIII protein is present at much lower abundance compared to other proteins on phage (e.g. pVIII is present at >1000-fold higher concentration), overall interpretation of gel is difficult. Large amounts of non-specific fluorescence is observed at the bottom of the gel; this may be associated with major coat protein pVIII, or could correspond to free fluorescein retained on the gel.

Figure 15:
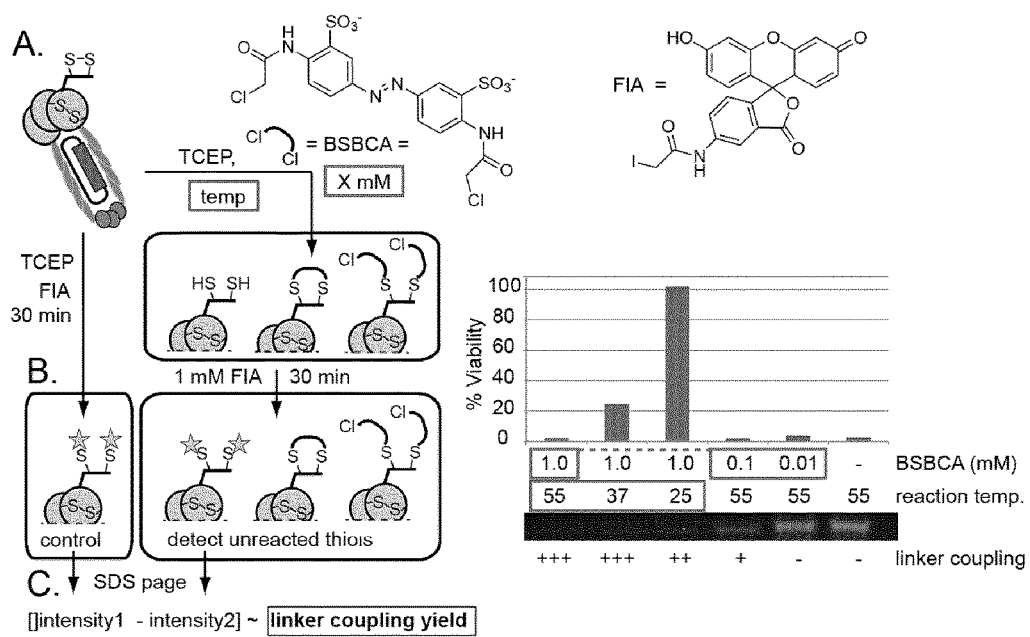
FIG. 15 illustrates the detection of the marker with linker using SDS-page gel electrophoresis.

FIG. 15 (A to C) illustrates the detection of the marker with linker using SDS-page gel electrophoresis. Phage was reacted with fluorescein iodoacetamide (FIA) before and after the reaction with the linker. Fluorescence after the reaction with linker indicates remaining unreacted groups (ie. an indication of efficiency of the linker coupling). The gel shows that coupling at lower concentrations of BSBCA linker does not work even at higher reaction temperatures. At high concentration of linker (1 mM), the reaction proceed equally well at 55° C. and room temperature.

Thus, it can be seen that the present method offers improved detection and quantification of derivatized peptides over conventional bulk methods.

Figure 16:
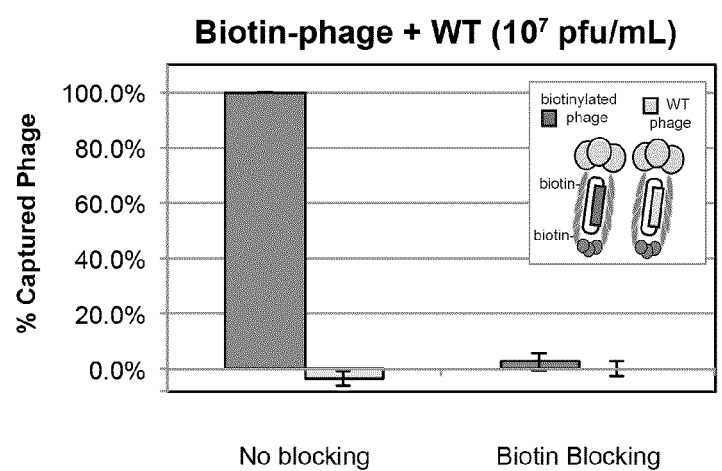
FIG. 16 illustrates an optimization of the capture of derivatized peptides by biotin/streptavidin interactions.

Example 5: Optimization of the Capture of Derivatized Peptides by Biotin/Streptavidin Interactions FIG. 16 illustrates an optimization of the capture of derivatized peptides by biotin/streptavidin interactions. Conditions were selected under which biotinylated phage was captured by magnetic bead (MB)-streptavidin quantitatively but capture of non-biotinylated phage was zero. Additionally, capture of biotinylated phage is biotin-specific; it does not occur if the MB-streptavidin is pre-blocked with soluble biotin.

Example 6: Optimization of Various Aldehyde Reactions on Phage

Figure 17:
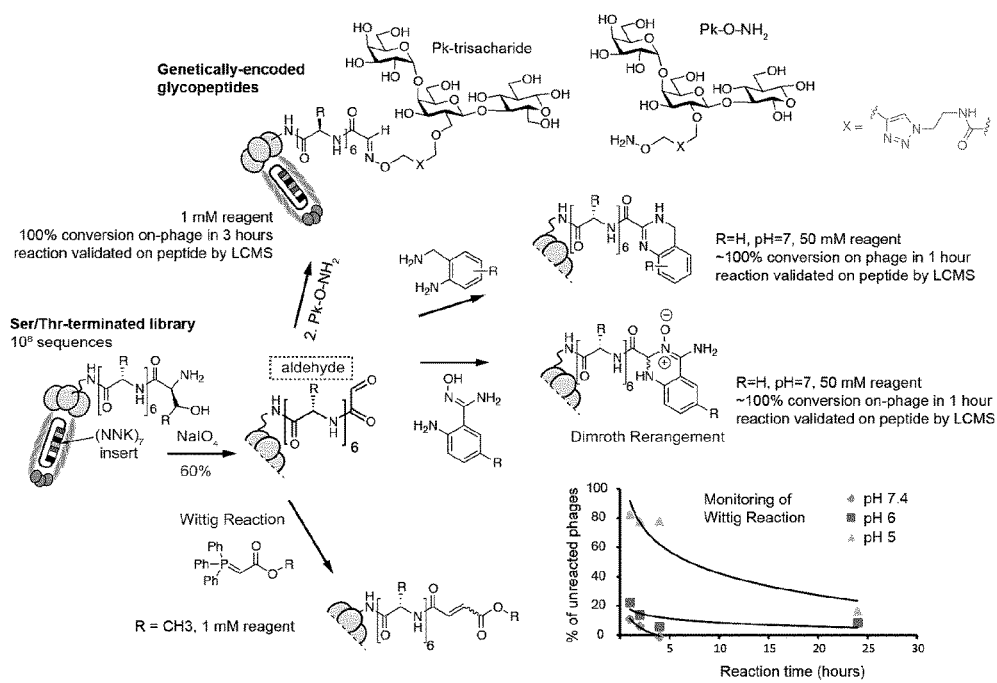
FIG. 17 illustrates the optimization of various aldehyde reactions on phage.

FIG. 17 illustrates the optimization of various aldehyde reactions on phage. In this figure, from top-to-bottom: oxime ligation of complex glycan, aminobenzylamine ligation/ Dimroth rearrangement Wittig reaction. In each case, the phage of library was oxidized to form aldehyde. The amount of aldehyde before and after reaction was characterized using biotin-hydroxylamine as described in FIG. 4. "100% conversion" means that no reactive aldehyde was detected after the incubation with the appropriate reagent. Conversion of the N-terminal aldehyde to the described structure was confirmed in an independent reaction on synthetic peptides in the same conditions (pH, concentration, buffer, temperature) monitored by liquid chromatography mass-spectrometry.

Figure 18:
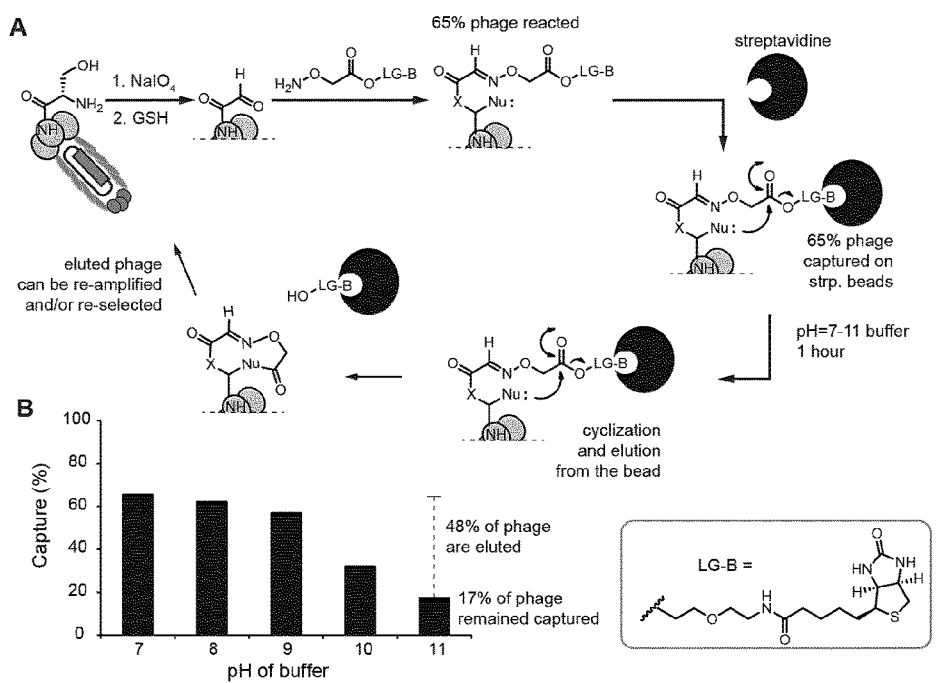
FIG. 18 shows an example of a step-wise cyclization reaction (A) and a graph showing % capture vs pH (B).

FIG. 18 shows an example of a step-wise cyclization reaction (A) and a graph showing % capture vs pH (B). In the first step, phage is modified by the linker that contains a detection marker, here biotin. In the second step, the detection marker is eliminated. Steps 1 and 2 can be quantified and selected independently. Unreacted molecules after step 1 can be discarded. Raising the pH promotes the second reaction (cyclization) and simultaneous elution of phage from beads. Only molecules reacted in step 2 can be carried to the next round. Provided example is reaction of phage-displayed aldehyde with molecule that contains a group ("group 1") that reacts with an aldehyde in reaction condition 1 (oxime, reacts at pH=4.7) and a leaving group, such as ester that reacts in reaction condition 2 (pH>8). Group 1 includes a hydroxylamine (or aminooxy group). Other groups that undergo reaction with aldehyde at pH<8 would be suitable. Examples of such groups are stabilized phosphor ylides (Wittig reaction), aminobenzamidoximes and aminobenzylamines.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A method of quantifying an amount of a macrocyclic peptide displayed on a phage by phage display, the method comprising:
   providing a phage containing a target peptide thereon;
   reacting the phage containing the target peptide with a first reagent to derivatize the target peptide to form a derivatized peptide,
   reacting the derivatized peptide with $^-C{\equiv}N^+$-biotin, thereby incorporating the $^-C{\equiv}N^+$-biotin within the derivatized peptide to form a macrocyclic peptide; and
   determining an amount of the detection marker, thereby quantifying the amount of the macrocyclic peptide displayed on the phage.

2. A method of quantifying an amount of a derivatized peptide displayed on a phage by phage display, the method comprising:
   providing a phage containing a target peptide displayed thereon;
   reacting the phage containing the target peptide with a first reagent to derivatize the peptide to form a derivatized peptide,
   reacting the derivatized peptide with a capture agent comprising a detection marker, thereby incorporating the detection marker within the derivatized peptide; and
   determining an amount of the detection marker, thereby quantifying the amount of the derivatized peptide displayed on the phage, wherein the capture agent is biotin-aldehyde reactive probe (ARP).

3. The method of claim 2, wherein the concentration of biotin-ARP is about 0.2-5 mM.

4. The method of claim 3, wherein the concentration of biotin-ARP is about 0.2 mM, 1 mM, or 5 mM.

* * * * *